US010463461B2

(12) United States Patent
Klemm et al.

(10) Patent No.: US 10,463,461 B2
(45) Date of Patent: *Nov. 5, 2019

(54) PERSONAL HYGIENE DEVICE WITH RESONANT MOTOR

(71) Applicant: Braun GmbH, Kronberg (DE)

(72) Inventors: Torsten Klemm, Frankfurt (DE); Kervin Küchler, Darmstadt (DE); Andreas Moehring, Kronberg (DE); Norbert Schaefer, Frankfurt (DE); Martin Stratmann, Bad Soden (DE); Carl Stückrath, Friedberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/045,991

(22) Filed: Jul. 26, 2018

(65) Prior Publication Data

US 2018/0325638 A1 Nov. 15, 2018

Related U.S. Application Data

(63) Continuation of application No. 15/461,422, filed on Mar. 16, 2017, now Pat. No. 10,058,408, which is a (Continued)

(30) Foreign Application Priority Data

Jun. 26, 2014 (EP) .................................... 14174206
May 27, 2015 (EP) .................................... 15169330

(51) Int. Cl.
*G05D 1/02* (2006.01)
*A61C 17/22* (2006.01)
(Continued)

(52) U.S. Cl.
CPC ............ *A61C 17/221* (2013.01); *A45D 26/00* (2013.01); *A61C 15/047* (2013.01); *A61C 17/20* (2013.01);
(Continued)

(58) Field of Classification Search
CPC ...... H02P 25/032; A61C 17/34; A61C 17/221
See application file for complete search history.

(56) References Cited

U.S. PATENT DOCUMENTS 5,019,764 A * 5/1991 Chang ................ G06K 7/10881
235/462.3
9,628,014 B2 4/2017 Klemm et al.
(Continued)

FOREIGN PATENT DOCUMENTS

WO WO2004034561 A1 4/2004

OTHER PUBLICATIONS

European Search Report for 1417206.4 dated Feb. 11, 2015.
(Continued)

*Primary Examiner* — Karen Masih
(74) *Attorney, Agent, or Firm* — Parker D. McCrary

(57) ABSTRACT

A personal hygiene device has a resonant motor and a motor control unit for applying a periodic voltage signal with a driving frequency at the resonant motor for driving the resonant motor into an oscillating motion with an oscillating frequency equal to the driving frequency. The motor control unit comprises a synthesizer circuit for digitally synthesizing the periodic voltage signal from voltage pulses of variable length provided with a pulse frequency higher than the driving frequency such that at least two voltage pulses are applied at least in one of two half cycles of each period of the periodic voltage signal.

18 Claims, 3 Drawing Sheets

Related U.S. Application Data continuation of application No. 14/749,557, filed on Jun. 24, 2015, now Pat. No. 9,628,014.

(51) Int. Cl.
  *H02P 25/032* (2016.01)
  *A61C 17/20* (2006.01)
  *A61C 17/34* (2006.01)
  *A45D 26/00* (2006.01)
  *A61C 15/04* (2006.01)
  *H02P 27/08* (2006.01)
  *A61B 17/24* (2006.01)
  *A61H 7/00* (2006.01)

(52) U.S. Cl.
  CPC ............ *A61C 17/34* (2013.01); *H02P 25/032* (2016.02); *H02P 27/08* (2013.01); *A45D 2026/008* (2013.01); *A61B 17/244* (2013.01); *A61C 17/3481* (2013.01); *A61H 7/00* (2013.01)

(56) References Cited

U.S. PATENT DOCUMENTS

| | | |
|---|---|---|
| 2003/0019937 A1 | 1/2003 | Colley et al. |
| 2006/0214611 A1 | 9/2006 | Wang et al. |
| 2010/0281636 A1 | 11/2010 | Ortins et al. |
| 2011/0005015 A1 | 1/2011 | Iwahori et al. |
| 2012/0171657 A1 | 7/2012 | Ortins et al. |

OTHER PUBLICATIONS

All Office Actions for U.S. Appl. No. 14/749,557, filed Jun. 24, 2015.

All Office Actions for U.S. Appl. No. 15/461,422, filed Mar. 16, 2017.

\* cited by examiner

PERSONAL HYGIENE DEVICE WITH RESONANT MOTOR

FIELD OF THE INVENTION

The present invention is concerned with a personal hygiene device having a resonant motor that is driven by a motor control unit into an oscillating motion.

BACKGROUND OF THE INVENTION

It is known that a resonant motor (i.e. a motor that can essentially be described as a spring-mass system having a resonant behavior such that the motor is particularly efficient when driven at or closely around its resonance frequency) can be driven into an oscillating motion by periodically applying an essentially rectangular voltage signal in every half cycle of a period of the oscillating motion, where the voltage signal is applied with alternating sign in the different half cycles of an individual period. The resonant motor may be arranged in the bridge section of an H-bridge circuit by which the applied voltage signal can be commuted, i.e. inverted, and motor current can be discharged from the motor coil prior to the change of the motion direction. Document WO 2004/034561 A1 generally discusses a resonant motor arranged in a bridge section of a H-bridge circuit and a driving scheme by applying rectangular voltage pulse signals at the motor by a motor control unit comprising the H-bridge circuit.

It is further known that resonant motors can be used in personal hygiene devices such as electric toothbrushes or electric shavers.

It is an object of the present disclosure to provide a personal hygiene device with a resonant motor that is improved over the known personal hygiene devices, in particular with respect to its noise behavior.

SUMMARY OF THE INVENTION

In accordance with one aspect there is provided a personal hygiene device comprising a resonant motor, a motor control unit for applying a periodic voltage signal with a driving frequency at the resonant motor for driving the resonant motor into an oscillating motion with an oscillating frequency equal to the driving frequency, wherein the motor control unit comprises a synthesizer circuit for digitally synthesizing the periodic voltage signal from voltage pulses of variable length provided with a pulse frequency higher than the driving frequency such that at least two voltage pulses are applied at least in one of two half cycles of each period of the periodic voltage signal.

BRIEF DESCRIPTION OF THE DRAWINGS

The proposed personal hygiene device will be further elucidated by a detailed description of example embodiments and by reference to figures. In the figures

DETAILED DESCRIPTION OF THE INVENTION

Figure 1:
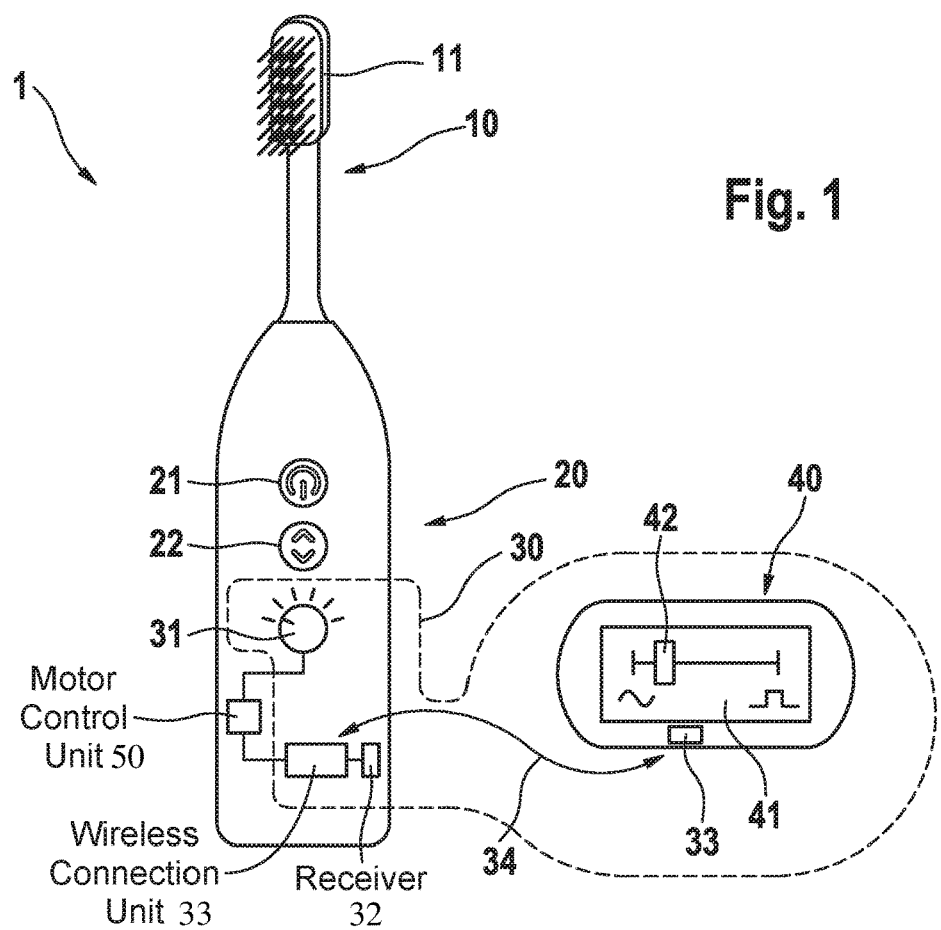
FIG. 1 is a schematic depiction of an example embodiment of a personal hygiene device in accordance with the present disclosure.

A "resonant motor" (or oscillating motor) in accordance with the present disclosure means a motor that has a resonant oscillation behavior. A resonant motor can be mathematically expressed as a harmonic oscillator, i.e. a spring-mass system. A resonant motor in accordance with the present disclosure is driven into oscillating motion by periodic application of an external force, in particular a periodic voltage signal as will be explained in the following paragraphs. The amplitude of the moving part of the resonant motor becomes maximal when the driving frequency of the external driving force is at the resonance frequency. Thus, a resonant motor can efficiently be driven with a driving frequency of the periodic voltage signal at or close to the resonance frequency of the resonant motor, even though driving the resonant motor with a periodic voltage signal having a driving frequency different to the resonance frequency is possible as well, but leads to a less efficient driving (more energy is needed for achieving the same amplitude as at the resonance frequency).

The resonant motor typically comprises a motor coil and at least one movable motor armature carrying at least one permanent magnet assembly having at least one permanent magnet fixedly connected with the motor armature. The motor armature is held in a rest position by at least one spring element. The resonant motor is driven into an oscillating motion by application of a periodic voltage signal (see below for a discussion of the periodic voltage signal) at the motor coil such that a current flow from a voltage source such as a battery or an accumulator through the motor coil is stimulated. The permanent magnet assembly of the motor armature interacts with the electromagnetic field that is generated by the current flowing through the motor coil. By this interaction, the motor armature, which is held in a rest position by means of the at least one spring element, is forced to move out of its rest position against the spring force of the at least one spring element. When the electromagnetic interaction ceases or changes its direction (e.g. the periodic voltage signal changes its sign between the two half cycles per period), the armature moves back towards its rest position and also beyond the rest position (until it reaches its maximum deflection amplitude) so that finally the armature is driven into an oscillatory motion by continuous periodic application of the voltage signal. The oscillatory motion occurs with the driving frequency at which the periodic voltage signal is applied at the resonant motor (i.e. the driving frequency determines the oscillation frequency of the oscillating motion of the resonant motor).

A "periodic voltage signal" in accordance with the present disclosure means a voltage signal that has periodically recurring non-zero voltage signal content to provide the external driving force for the motor. As the frequency of the periodically recurring voltage signals determines the oscillation frequency of the resonant motor, the periodic voltage signal has a period that is divided into two equally long half-cycles. In some embodiments, a non-zero voltage signal is present in both half cycles (but with opposite signs to drive the resonant motor in the two oscillation directions), but it is not necessary to drive the resonant motor in both half cycles. In some embodiments, the periodic voltage signal has a non-zero voltage signal only in one of the two half-cycles of each period. While the periodic voltage signal might be a P-periodic function (P being the period) in a mathematical sense, i.e. (f(x+P)=f(x)), this is not necessary and also often not productive as the resonant motor may need varying driving force in consecutive periods under different load conditions to oscillate with an essentially constant amplitude. What remains constant is the period of the recurrence of the voltage signals, i.e. the length of the period and of the half cycles (or in other words: the driving frequency), which shall not exclude that the driving frequency can be influenced by a user as will be explained further below. It is also not necessary that the time-integral over the voltage signal is identical for both half cycles (i.e. the energy fed to the resonant motor may be different in the two half cycles of aperiod), as was already made clear with respect to driving the resonant motor by applying a non-zero voltage signal in only one of the half cycles. In some embodiments, the time integrals over the voltage signals in the two half cycles are finite but different.

Thus, in some embodiments the voltage signals applied at the resonant motor in the two half cycles per period of the periodic voltage signal have opposite signs and further in particular the voltage signal applied in one half cycle has different sign but same absolute voltage level than the voltage signal applied in the other half cycle, which shall not exclude embodiments in which the absolute voltage levels in the two half cycles are not identical. In some embodiments, the periodic voltage signal has zero voltage in one of the half cycles (similar to the excitation function that a person applies at a swing, where also only energy is applied at the swing in one movement direction). Providing a periodic voltage signal that has zero voltage in one of its half cycles has been found to be less energetically efficient than applying a voltage signal in both half cycles.

For sake of clarity, the driving of a resonant motor is different to the driving of a DC motor, where the frequency of an applied voltage signal does not determine the rotation frequency, but where the rotation frequency is depending on a height of a voltage applied at the DC motor (e.g. US 2011/005015 A1 describes a DC motor that is driven into a rotation by application of an average voltage signal provided by a PWM signal of a certain duty cycle—the higher the duty cycle of the PWM signal—i.e. at constant frequency of the PWM pulses—, the higher is the rotation frequency). In US 2011/005015 A1 two different rotation frequencies of the DC motor are used to excite different mechanical resonant modes of a replacement brush. The DC motor itself is not a resonant motor.

The driving frequency in the present disclosure may typically be at or close to the resonance frequency of the resonant motor in order to achieve high efficiency. But obviously, this is just an efficiency consideration and the resonant motor can virtually be driven at any driving frequency (with reduced efficiency), which driving frequency in turn leads to an oscillating motion of the resonant motor having an oscillation frequency that is equal to the driving frequency.

The moving permanent magnet assembly also induces a voltage across the motor coil and thus a current flow through the motor coil, which induced electric current flow typically is smaller than the electric current flow from the voltage source. The induced voltage is a measure for the velocity of the armature and due to the direct relationship also for the amplitude of the armature. The previously mentioned document WO 2004/034561 A1, which shall be incorporated herein by reference, generally describes how a resonant motor is driven in particular by an alternating periodic voltage signal. The armature of the resonant motor may in particular be arranged for a linear reciprocating movement or for an oscillating rotating movement.

It is generally known (e.g. from document WO 2004/034561 A1) to drive a resonant motor by applying a periodic voltage signal that comprises only a single voltage signal of a certain duty period per half cycle (where the length of the duty cycle may be controlled to compensate for different load situations). I.e. if the oscillation frequency of the resonant motor is $f_o$ (e.g. in a non-limiting example $f_o$ is 100 Hz), than the driving frequency $f_d$ may be set to $f_o$, i.e. $f_d=f_o$. A full cycle of the periodic voltage signal (and hence also of the oscillating motion of the resonant motor) thus last 0.01 seconds and a half cycle 0.005 seconds. In this known example, one voltage pulse is provided per half cycle, so that a pulse frequency of the periodic voltage signal is twice as high as the driving frequency, i.e. $f_p=2 \cdot f_d$. It has now been found that a resonant motor can be driven into a much smoother and more silent oscillating motion if instead of a single voltage pulse per half cycle of the oscillating motion, the applied periodic voltage signal approximates a sine-wave voltage signal or another similar function at least for a certain fraction of a cycle of the periodic voltage signal.

In some embodiments discussed herein, the voltage signal (that otherwise approximates a continuous, e.g. sinusoidal function) may be set to zero for a certain time span in some half cycles—e.g. in the first half cycle of each 5th period of the applied periodic voltage signal—or the voltage may be set to zero for a certain time span in one of the two half cycles of each period (this half cycle may always be the first or the second half cycle or this half cycle may alternate between the first and the second half cycles). The time span during which the voltage signal is then set to zero may be chosen to allow measuring the mentioned induced voltage in the motor coil at otherwise zero external current flow in order to achieve a parameter indicative of the velocity and amplitude of the moving motor armature of the resonant motor and thus to allow controlling the periodic voltage signal such that a constant amplitude is achieved even under changing load conditions.

A personal hygiene device with a resonant motor in accordance with the present disclosure has a motor control unit that can provide a selectable (digitally synthesized) periodic voltage signal at the resonant motor; in particular the periodic voltage signal may be selected to be a sinusoidal voltage signal. An ideal sinusoidal voltage signal does not comprise any harmonics and thus tends to lead to a smoother operation of the overall personal hygiene device and noise and vibrations that are caused by harmonics are efficiently reduced. The synthesizer circuit in accordance with the present disclosure digitally synthesizes a smooth periodic voltage signal from a high number of voltage pulses of variable length, where the voltage pulses are provided at a pulse frequency higher than the driving frequency so that at least in one of the half cycles per period two voltage pulses are provided (hence, the pulse frequency is then at least four times higher than the driving frequency). The pulse frequency is determined by the constant (temporal) distance between the voltage pulses. In some embodiments, the pulse frequency is at least six times higher than the driving frequency (i.e. the voltage signal in each half cycle is approximated by at least three voltage pulses), optionally at least 20 times higher (at least 10 pulses per half cycle) and further optionally at least a 100 times higher (at least 50 pulses per half cycle) than the driving frequency. While the voltage signal as generated comprises individual pulses, the characteristics (e.g. capacitance and inductance) of the motor filter the pulses such that the motor "sees" a continuous voltage signal. Even though a digitally synthesized sinusoidal voltage signal as described does not necessarily result in an ideal sinusoidal signal, it had been found that noise reductions of up to −10 dB can be achieved between driving a resonant motor of a personal hygiene device with a rectangular driving function (i.e. a single rectangular voltage pulse applied per half cycle of the periodic voltage signal) and with an almost sinusoidal voltage signal that is digitally synthesized as herein described. A sinusoidal voltage signal also leads to a sinusoidal current flow through the motor coil. It shall be understood that the approximation quality of a digitally synthesized periodic voltage signal (details of the voltage signal synthesis are described further below) vs. an ideal sinusoidal voltage signal depends on, e.g., the pulse frequency to driving frequency ratio and thus also only an approximate sinusoidal current results. During each voltage pulse, a current flow into the coil builds up and if the voltage pulse is interrupted until the next voltage pulse is provided, then the charge stored in the coil flows out of the coil to a certain extend.

A personal hygiene device in accordance with the present disclosure may be an electric toothbrush, an electric tongue cleaner, an electric flossing device, an electric shaver, an electric hair removal device, an electric skin massaging device or the like.

FIG. 1 is a schematic depiction of a personal hygiene device 1 in accordance with the present description. The personal hygiene device 1 is here realized as an electric toothbrush, which shall not be considered as limiting. The personal hygiene device 1 generally comprises a head section 10 that is driven into an oscillatory motion (either the whole head section 10 is driven into such an oscillatory motion or the head section 10 comprises a head element 11 that is driven into the oscillatory motion) by a resonant motor (see FIG. 2) provided in a handle section 20 of the personal hygiene device 1. The personal hygiene device 1 may have an on/off switch 21 and optionally a mode selector button 22, even though the personal hygiene device 1 may not necessarily need to have these features (e.g. the personal hygiene device 1 may be arranged to automatically switch on the resonant motor if the head 11 is close to tissue, which may be detected by a capacitive threshold sensor and/or the personal hygiene 1 has no switchable modes or a mode selection may be implemented in another manner, e.g. via voice recognition).

In some embodiments, the personal hygiene device 1 has a user controllable input unit 30 for providing user-selected input influencing the periodic voltage signal applied at the resonant motor via a motor control unit 50 as will be explained in more detail further below. Generally, the user may be able to influence the shape of the periodic voltage signal or the frequency of the periodic voltage signal, the frequency of the pulses used to approximate the ideal periodic voltage signal (see below) etc. In some embodiments, the user controllable input unit 30 has a control element 31 via which a user can selectively influence the periodic voltage signal applied at the resonant motor via the motor control unit. Additionally or alternatively, the user controllable input unit 30 may comprise a separate control device 40 (i.e. a separate control device physically separate from the handle section 20). The personal hygiene device may then comprise a wireless connection unit 33 for establishing a wireless connection 34 between the separate control device 40 and the handle section 20 so that e.g. data can be communicated in a wireless fashion from the separate control device 40 to the handle section 20 and thus to the motor control unit 50. The wireless connection 34 may in particular be realized as a Bluetooth connection, but other wireless connection standards are as well possible, e.g. an IEEE 802.11 radio frequency connection or a proprietary wireless connection. Generally, the separate control device 40 comprises a control element 42 via which the user can influence the periodic voltage signal used for driving the resonant motor. The control element 42 may be realized as a switch or selector button, a slider or the like. In some embodiments, the separate control device 40 comprises a touch-sensitive screen 41 on which a virtual control element 42 can be displayed, which can be tuned by touching the screen 41 with a finger and sliding the finger over the screen. In the shown example, the virtual control element 42 is realized as a virtual slider by which the user can influence the periodic voltage signal to be applied at the resonant motor, e.g., the user can set whether the periodic voltage signal has a sinusoidal shape or a rectangular shape and potentially the user can set at least one further shape of the periodic voltage signal having a more intermediate character between a sinusoidal shape and a rectangular shape. In some embodiments, the separate control device 40 is realized by a smart phone, by a tablet computer or any other mobile appliance. The separate control device 40 may then have a software module (such as a mobile application software or "app") provided for realizing the virtual control element 42 and for transmitting the setting chosen by a user from the separate control device 40 to a receiver 32 in the handle section 20. As the shape of the periodic voltage signal tends to influence the noise characteristic of the personal hygiene device 1 during operation, such a user controllable input device 30 as described allows a user to set a personally favored periodic voltage signal, e.g. a periodic voltage signal that generates less (or more) noise (or sound) than the standard periodic voltage signal set by the manufacturer of the personal hygiene device 1. E.g. the manufacturer may have chosen a periodic voltage signal at which the energy consumption of the resonant motor is relatively low but where the noise or sound level of the personal hygiene device is at a medium level or where the noise or sound of the personal hygiene device is perceived by an individual user as less favorable due to spectral components in the noise or sound than the noise or sound generated with a different periodic voltage signal. Some users may favor less noise as they get annoyed by the noise, while other users may favor more noise as they connect the sound of the personal hygiene device with its hygienic properties (e.g. in case of an electric toothbrush, a high sound level may be assigned to a high presumed cleaning power). The influencing possibilities described above with respect to a separate control device can also be applied in case of a user controllable input unit that is not separate and is, e.g., realized as a part of the handle section of the personal hygiene device.

Figure 2:
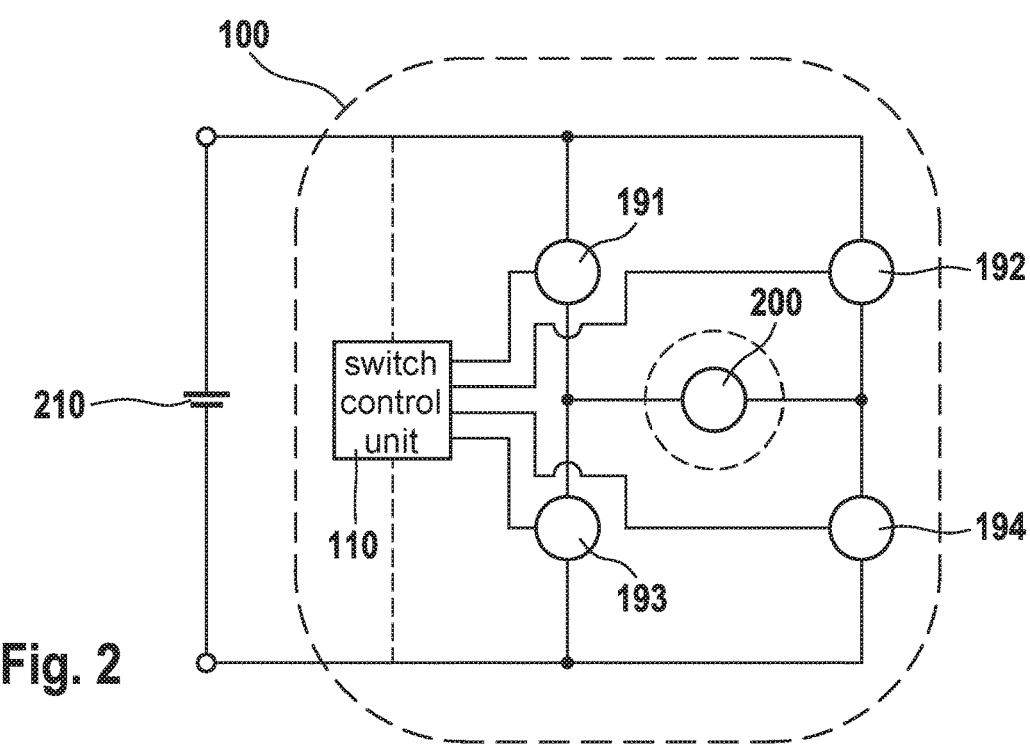
FIG. 2 is a schematic depiction of a motor control unit for driving a resonant motor.

FIG. 2 is a schematic depiction of a motor control unit 100 for driving a resonant motor 200 (which may be disposed in a handle section of the personal hygiene device as was mentioned before) into an oscillating motion, e.g. a linear reciprocating motion or an oscillating rotation or a mixture thereof. The resonant motor 200 is arranged in the bridge section of an H-bridge (or: full bridge) circuit comprising four switches 191, 192, 193, and 194. The switches of the H-bridge circuit are controlled by a switch control unit 110 and, as has been discussed in previously mentioned document WO 2004/034561 A1, a voltage supplied from a voltage source 210 can then be applied in a positive direction by switching on switches 191 and 194 and switching off switches 192 and 193 and in a negative direction by switching on switches 192 and 193 and by switching off switches 191 and 194. It is as well possible to short-circuit the resonant motor 200 by, e.g., switching on switches 193 and 194 and switching off switches 191 and 192 (again, as is described in document WO 2004/034561 A1). The switches 191 to 194 may each be realized by a field effect transistor (FET), in particular by a MOSFET. The switches 191 to 194 may in particular each comprise an in parallel connected protection diode for protecting the respective switch from overvoltage. The switches 191 to 194 are also chosen such that they can be switched with the pulse frequency required by the motor control unit 100, e.g. 30 kHz as one non-limiting example.

While document WO 2004/034561 A1 describes that a single voltage pulse is applied at the resonant motor in each half cycle of each period, the herein proposed motor control unit 100 comprises a synthesizer circuit for providing voltage pulses of varying pulse length at the resonant motor at a pulse frequency that is at least four times higher than the driving frequency at which the resonant motor is driven. The idea behind the application of voltage pulses at a respectively high pulse frequency is to model a target shape of the average periodic voltage signal by the voltage pulses having essentially constant height (the voltage height may be determined by a voltage source) but varying pulse length (digital synthesis). An (ideal) sinusoidal periodic voltage signal would then lead to a sinusoidal current flow through the motor coil, as had previously been explained. Typically, a resonant motor in a personal hygiene device may be driven at a driving frequency of between about 50 Hz to about 500 Hz, which shall not exclude other driving frequency values. Electric toothbrushes are often driven at a frequency of between about 65 Hz to about 300 Hz. As a non-limiting example, a driving frequency of 150 Hz may be used. The pulse frequency is given by the constant temporal distance between consecutive voltage pulses; the pulses may have varying pulse length in order to model the target shape of the periodic voltage signal. The pulse frequency should be at least four times higher than the driving frequency, in particular the pulse frequency is at least 6 times higher than the driving frequency (at least three voltage pulses are then applied per half cycle), optionally the pulse frequency is at least 20 times higher than the driving frequency (at least ten voltage pulses are then applied per half cycle) and further optionally the pulse frequency is at least a hundred times higher than the driving frequency (at least 50 voltage pulses are then applied per half cycle). E.g. at a driving frequency of 150 Hz, the pulse frequency may then be at least 900 Hz, at least 3 kHz, or at least 15 kHz. Generally, the pulse frequency may be above 18 kHz and optionally above 20 kHz in order to shift the pulse frequency into a non-audible (for the human ear) frequency range. The pulse frequency may be chosen to be below 100 kHz.

In accordance with the present disclosure, the motor control unit provides via its synthesizer circuit voltage pulses of variable length at the resonant motor. In order to allow a sensible shaping of the average periodic voltage signal, the length of each voltage pulse should be controllable with sufficient resolution, which requires that the voltage pulse length can be controlled at a clocking frequency of the motor control unit that is higher than the pulse frequency, e.g. 128 times higher (resulting in a 7 bit resolution of the voltage pulse) or 256 times higher (8 bit resolution) (even though higher or lower resolutions such as 9 bit or 10 bit or 6 bit or 5 bit or 4 bit etc. shall not be excluded). E.g. at 15 kHz pulse frequency, the clocking frequency would be 3.84 MHz for an 8 bit resolution. As another example, the driving frequency is 150 Hz, the pulse frequency is 30 kHz and the resolution is 7 bit (again leading to a clocking frequency of 3.84 MHz).

Figure 3:
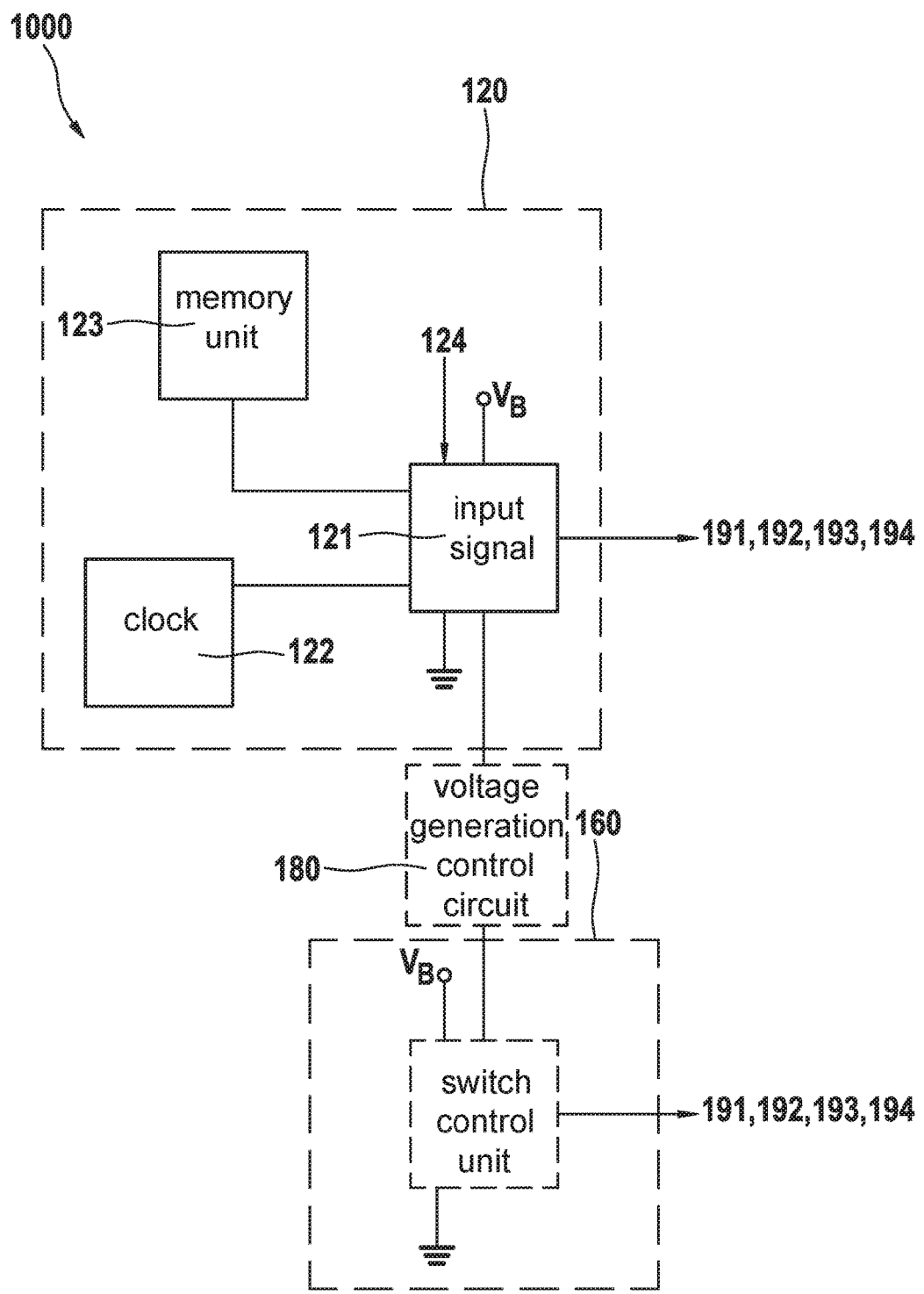
FIG. 3 is a schematic depiction of a motor control unit comprising a synthesizer circuit for digitally synthesizing a periodic voltage signal for driving a resonant motor.

FIG. 3 is a schematic depiction of an example motor control unit 1000 having an example synthesizer circuit 120 in accordance with the present disclosure. The synthesizer circuit 120 as shown comprises a switch control unit 121 for switching switches 191 to 194 of an H-bridge as shown in FIG. 2, a clock 122 for proving a clocking frequency (e.g. 3.84 MHz) and a memory unit 123. The memory unit 123 may in particular comprise at least one look-up table of normalized voltage pulse length values to be applied during one half cycle or during one period of the periodic voltage signal. In case that the voltage signal applied during the second half-cycle is identical but inverted to the voltage signal applied during the first half cycle of each period, then it is sufficient to just provide the voltage pulse length values for the first half-cycle (the switches of the H-bridge are used to invert the sign of the voltage applied at the resonant motor). In some embodiments, the memory unit 123 comprises at least two look-up tables of voltage pulse length values, e.g. one look-up table for a sinusoidal periodic voltage signal and one look-up table for a rectangular periodic voltage signal. In some embodiments, three or more look-up tables are provided, where e.g. the third look-up table provides voltage pulse length values for a periodic voltage signal resembling an intermediate shape between a sinusoidal and a rectangular shape. In some embodiments, two, three or more such as five or ten etc. look-up tables are provided for intermediate periodic voltage signal shapes such that a user could finely tune (via the previously described user controllable input device) the shape of the periodic voltage signal to lie between a sinusoidal and a rectangular shape. The synthesizer circuit 120 may therefore be arranged to receive an input signal 124 from the user controllable input device 30 discussed with reference to FIG. 1. In some embodiments, at least one look-up table is provided for generating a periodic voltage signal different to a sinusoidal or rectangular shape (or an intermediate shape between those two), e.g. for generating a periodic triangle signal, a periodic trapeze signal, or a periodic saw tooth signal, even this list shall not be considered as closed and any other periodic voltage signal shape may be employed as well. If a separate control device as discussed with reference to FIG. 1 is used, the respective application software module may be arranged to allow the user to freely define an arbitrary periodic voltage signal shape. The synthesizer circuit 120 may be realized as a direct digital synthesis (DDS) circuit (e.g. the user may be allowed to draw the shape with a finger gliding over a touch sensitive display). As a non-limiting example, at least part of the synthesizer circuit 120 may be realized by the low power DDS AD9838 chip (or a similar IC) available from Analog Devices, Norwood, Mass., USA. In other embodiments, the synthesizer circuit is realized (optionally together with the switches of the H-bridge) as an integrated circuit (IC), in particular an application specific IC (ASIC). In addition or alternatively, the synthesizer circuit may comprise a computing unit that computes the voltage pulse length values for, e.g., a sinusoidal voltage function in real time instead of using a look-up table.

In some embodiments and indicated in FIG. 3 with dashed lines, the motor control unit 1000 additionally comprises a digital voltage circuit 160 that is arranged for providing a single rectangular voltage pulse per half cycle at the resonant motor as is known from prior art. A voltage generation control circuit 180 may be provided for selectively switching on either the synthesizer circuit 120 or the digital voltage circuit 160. Both, the synthesizer circuit 120 and the digital voltage circuit may thus be coupled with switches 191, 192, 193, 194 of an H-bridge, and the voltage generation control circuit 180 would selectively allow only one of these two circuits 120, 160 to control the switches. In some embodiments, the synthesizer circuit 120 may be used to provide a first part of a periodic voltage signal by a plurality of short voltage pulses (e.g. an upwards voltage ramp) and then the voltage generation control circuit 180 switches to the digital voltage circuit 160 to generate a single long voltage pulse as a second part of the periodic voltage signal per half cycle. Optionally, a third part of the voltage signal may then again be applied by the synthesizer circuit 120, e.g. a downwards voltage ramp so that, e.g., a trapeze signal is generated together with the upwards ramp and the long voltage pulse. Obviously, long rectangular voltage signals can as well be shaped by a synthesizer circuit instead of an analog voltage circuit. It should also be understood that instead of applying voltage pulses via switching the switches 191 to 194 of the H-bridge (see FIG. 2), a periodic voltage signal generated by a synthesizer circuit can be directly applied at the resonant motor (the synthesizer circuit would then comprise the necessary switches for switching the voltage pulses from which the periodic voltage signal is synthesized).

Figure 4:
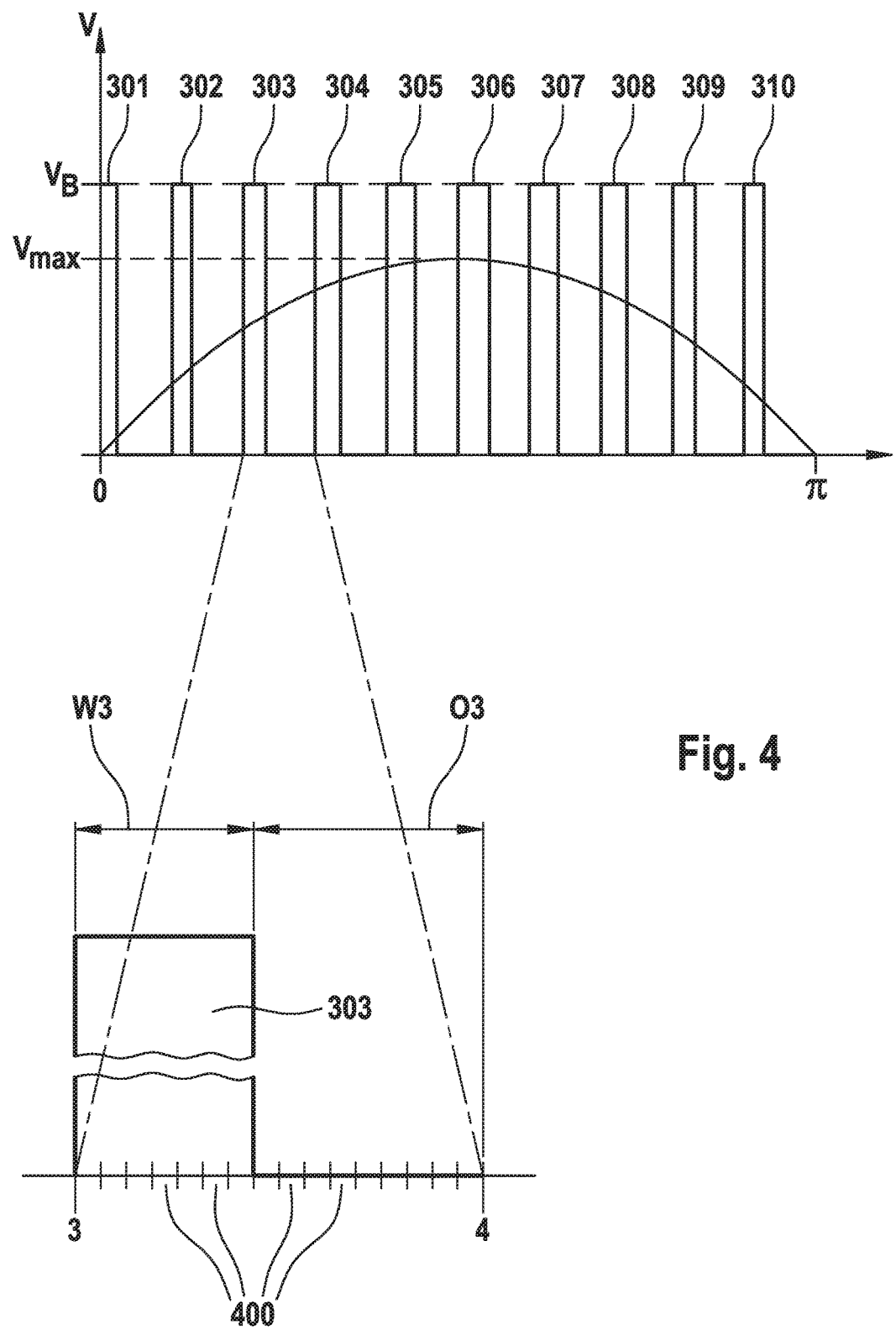
FIG. 4 is a schematic depiction of a half-cycle of a sinusoidal periodic voltage signal composed from voltage pulses of variable length.

FIG. 4 is a schematic depiction of an example sinusoidal periodic voltage signal generated from a plurality of short voltage pulses of variable length but constant height, where only the first half-cycle of a period of the approximate sinusoidal periodic voltage signal applied at the resonant motor is shown. It is understood that the second half-cycle may have the same functional behavior but with an inverted voltage sign. In FIG. 4, the first half-cycle of the sinusoidal periodic voltage signal is exemplary generated by applying 10 voltage pulses 301 to 310 (i.e. the pulse frequency is 20 times the driving frequency, e.g. at 150 Hz driving frequency this leads to a 3 kHz pulse frequency). As had been explained above, the voltage pulse length values for each of the voltage pulses 301 to 310 may be provided as tabularized values in a memory unit and may have been predetermined so that in average an approximate sinusoidal voltage results. FIG. 4 comprises a magnification of the third voltage pulse 303 and it is indicated by sixteen (16) tick marks 400 that the resolution in the shown case is four (4) bit (this is a non-limiting example and was also chosen for presentability of the general concept), so that a clocking frequency of 48 kHz is needed in this example case. In the schematic depiction, the third voltage pulse 303 has a pulse length W3 of seven clocking frequency periods and then a voltage off length O3 of nine clocking frequency periods follows (until the fourth voltage pulse 304 is switched on). As is also indicated in FIG. 4, the maximum voltage $V_{max}$ provided at the resonant motor may be lower than the available voltage $V_B$ from the voltage source (e.g. $V_{max}$ could be 60% of $V_B$). This allows increasing the voltage level at the resonant motor under a load condition when the resonant motor requires more energy to provide the same oscillatory amplitude (e.g. the tabularized voltage length values may then be increased by a conversion factor >1 reflecting the load state).

As has been explained in the previous paragraph, a load applied at the resonant motor may lead to reduced motion amplitude if the energy provision is not adequately adapted. The motor load of a resonant motor can be determined by determining the back EMF voltage of the motor (i.e. the voltage that is induced in the motor coil by the moving permanent magnet assembly of the moving armature) as the induced voltage is a measure of the velocity of the armature (which in turn is a measure of the amplitude of the armature movement as the oscillation frequency of course stays constant under varying load as it is given by the driving frequency). One method to determine this induced voltage is to provide a further coil positioned close to the armature, which involves further costs and further parts. Another method is to measure the back EMF at the motor coil when essentially no motor current flows (as then the applied voltage as well as the self-induced voltage are essentially reduced to zero). But if a sinusoidal periodic voltage signal is provided as driving signal at the motor coil, a sinusoidal current results and thus there is no time slot during the period at which no current flows through the motor coil. In some embodiments it is thus proposed to switch off the sinusoidal or any other continuous (or semi-continuous) driving signal at least during one of the half cycles of each period or of each $5^{th}$ or $10^{th}$ etc. period at least for a time period that allows the motor current to drop to zero and to stay at zero until a measurement of the back EMF has been made. The motor may be short circuited to achieve a fast current discharge. In some embodiments, the provision of voltage pulses is resumed in the same half cycle in which the provision of voltage pulses was stopped after the measurement of the back EMF was made. This may lead to the generation of harmonics due to switching on a voltage of a relatively high value after having provided a zero voltage. In some embodiments, the voltage pulse provision is switched off in the complete second quadrant of the half cycle in which the voltage is switched off. It had been found that this represents a good balance between current consumption and noise generation on the one hand and reliability of the back EMF measurement on the other hand.

Due to manufacturing tolerances, a resonant motor may not always have the same resonance frequency, which may be determined at the end of assembling the resonant motor by the manufacturer. In some embodiments, it may be considered important to always have the same difference between the resonance frequency of the resonant motor and the driving frequency applied by the motor control unit, it may become necessary to apply a different driving frequency than originally planned. E.g. a driving frequency of 150 Hz may have been planned and respectively 100 voltage pulse length values had been provided for a half cycle in the memory unit of the synthesizer circuit. But due to differences in the resonance frequency of the resonant motor, the driving frequency may need to lie in a range of between about 145 Hz to about 155 Hz. In the given example, a single voltage pulse relates to about 0.75 Hz so that in case that a reduced driving frequency of 145 Hz is to be employed, 103.45 pulses need to be employed per half-cycle (it is assumed that the clocking frequency as well as the pulse frequency are fixed values). In order to cope with this situation, the driving frequency may e.g. be set to about 144.75 Hz and 7 voltage pulse length values could be employed twice per period (in case of a required higher driving frequency, some voltage pulses may be omitted). This allows using the available look-up tables also for other frequencies. In some embodiments, the user may be allowed to influence the driving frequency via a user controllable input unit.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal hygiene device comprising
    a resonant motor;
    a motor control unit for applying a periodic voltage signal with a driving frequency at the resonant motor for driving the resonant motor into an oscillating motion with an oscillating frequency equal to the driving frequency;
    a separate control device connected to the motor control unit via wireless data communication;
    wherein the motor control unit comprises a synthesizer circuit for digitally synthesizing the periodic voltage signal from voltage pulses of variable length provided with a pulse frequency higher than the driving frequency and wherein a shape of the periodic voltage signal can be influenced by a user via the separate control device.

2. The personal hygiene device of claim 1, wherein the separate control device comprises a control element for selectively influencing the periodic voltage signal.

3. The personal hygiene device of claim 2, wherein the control element is arranged at a handle section of the personal hygiene device.

4. The personal hygiene device in accordance with claim 1, wherein the separate control is physically separate from a handle section of the personal hygiene device and the personal hygiene device further comprises a wireless connection unit for establishing a wireless connection between the handle section and the separate control device.

5. The personal hygiene device in accordance with claim 4, wherein the separate control device, in particular a smart phone or a tablet computer, has a control element for selectively influencing the periodic voltage signal, in particular the shape of the periodic voltage signal.

6. The personal hygiene device in accordance with claim 1, wherein the synthesizer circuit comprises a memory unit in which at least one look-up table of voltage pulse length values for at least one half-cycle of the periodic voltage signal is stored.

7. The personal hygiene device in accordance with claim 1, wherein the synthesizer circuit comprises a memory unit in which at least two look-up tables that each comprise voltage pulse length values for at least one half-cycle of the periodic voltage signal are stored and the separate control device is arranged to influence which look-up table is used to generate the periodic voltage signal.

8. The personal hygiene device in accordance with claim 1, wherein the pulse frequency of the synthesizer circuit is at least 6 times as high as the driving frequency, optionally wherein the pulse frequency of the synthesizer circuit is at least 20 times as high as the driving frequency and further optionally wherein the pulse frequency is at least 100 times as high as the driving frequency.

9. The personal hygiene device in accordance with claim 1, wherein the pulse frequency is above 18 kHz, optionally wherein the pulse frequency is above about 20 kHz and further optionally below 100 kHz.

10. The personal hygiene device in accordance with any one of claim 1, wherein a clocking frequency of the synthesizer circuit is at least 32 times the pulse frequency, optionally at least 128 times the pulse frequency, and further optionally at least 256 times the pulse frequency.

11. The personal hygiene device in accordance with claim 1, wherein the periodic voltage signal is one of a sine wave signal, a triangle signal, a trapeze signal, or a saw-tooth signal.

12. The personal hygiene device in accordance with claim 1, wherein the motor control unit comprises a digital voltage circuit for providing a single voltage pulse per half cycle at the resonant motor.

13. The personal hygiene device in accordance with claim 12, wherein the motor control unit is arranged to compose the periodic voltage signal by selectively switching between the synthesizer circuit and the digital voltage circuit, and wherein said selective switching happens at least once during at least one half cycle per period of the periodic voltage signal.

14. The personal care device of claim 1, wherein the motor control unit is arranged to switch off a driving signal during at least one of the half cycles of each period.

15. The personal care device of claim 14, wherein the motor control unit is arranged to cause the driving signal to stay at zero until a measurement of the back EMF has been made.

16. The personal care device of claim 14, wherein the motor control unit is arranged to short-circuit the motor to achieve a fast current discharge.

17. The personal care device of claim 15, wherein the motor control unit is arranged to have, after the measurement of the back EMF has been made, the voltage pulses resumed in the same half cycle in which the voltage pulses were stopped.

18. The personal care device of claim 15, wherein the motor control unit is arranged to cause the voltage pulsed switched off in a complete second quadrant of the half cycle in which the voltage is switched off.

* * * * *